(12) United States Patent
Waugh et al.

(10) Patent No.: US 8,425,607 B2
(45) Date of Patent: Apr. 23, 2013

(54) ANCHOR MEMBER LOCKING FEATURES

(75) Inventors: Lindsey G. Waugh, Memphis, TN (US); Jason A. Edie, Memphis, TN (US); Matthew D. Schultz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1502 days.

(21) Appl. No.: 11/695,939

(22) Filed: Apr. 3, 2007

(65) Prior Publication Data

US 2008/0249575 A1    Oct. 9, 2008

(51) Int. Cl.
*A61F 2/44* (2006.01)

(52) U.S. Cl.
USPC ........................... 623/17.16; 606/246

(58) Field of Classification Search ..... 623/17.11–17.16
See application file for complete search history.

(56) References Cited

U.S. PATENT DOCUMENTS

| | | | |
|---|---|---|---|
| 4,904,261 A | 2/1990 | Dove et al. | |
| 5,397,364 A | 3/1995 | Kozak et al. | |
| 5,578,034 A * | 11/1996 | Estes | 606/281 |
| 5,643,265 A * | 7/1997 | Errico et al. | 606/70 |
| 5,876,402 A * | 3/1999 | Errico et al. | 606/287 |
| 5,888,223 A | 3/1999 | Bray, Jr. | |
| 5,931,838 A | 8/1999 | Vito | |
| 6,235,059 B1 | 5/2001 | Benezech et al. | |
| 6,258,089 B1 * | 7/2001 | Campbell et al. | 606/86 B |
| 6,261,291 B1 | 7/2001 | Talaber et al. | |
| 6,331,179 B1 | 12/2001 | Freid et al. | |
| 6,342,074 B1 * | 1/2002 | Simpson | 623/17.11 |
| 6,468,311 B2 | 10/2002 | Boyd et al. | |
| 6,533,786 B1 | 3/2003 | Needham et al. | |
| 6,579,290 B1 | 6/2003 | Hardcastle et al. | |
| 6,592,586 B1 | 7/2003 | Michelson | |
| 6,602,255 B1 | 8/2003 | Campbell et al. | |
| 6,613,091 B1 | 9/2003 | Zdeblick et al. | |
| 6,629,998 B1 * | 10/2003 | Lin | 623/17.11 |
| 7,001,389 B1 | 2/2006 | Navarro et al. | |
| 7,025,769 B1 | 4/2006 | Ferree | |
| 7,033,394 B2 * | 4/2006 | Michelson | 623/17.11 |
| 7,794,482 B2 * | 9/2010 | Mathieu et al. | 606/290 |
| 7,909,859 B2 * | 3/2011 | Mosca et al. | 606/289 |
| 2002/0022843 A1 | 2/2002 | Michelson | |
| 2002/0099376 A1 | 7/2002 | Michelson | |
| 2002/0151899 A1 | 10/2002 | Bailey et al. | |
| 2002/0169508 A1 | 11/2002 | Songer et al. | |
| 2003/0078583 A1 | 4/2003 | Biedermann et al. | |
| 2004/0015169 A1 * | 1/2004 | Gause | 606/63 |
| 2004/0030338 A1 | 2/2004 | Paul | |
| 2005/0071006 A1 | 3/2005 | Kirschman | |
| 2005/0177236 A1 * | 8/2005 | Mathieu et al. | 623/17.11 |
| 2005/0192577 A1 | 9/2005 | Mosca et al. | |
| 2005/0216081 A1 * | 9/2005 | Taylor | 623/17.11 |
| 2006/0085071 A1 | 4/2006 | Lechmann et al. | |

\* cited by examiner

FOREIGN PATENT DOCUMENTS

WO    WO 00/78238    12/2000

OTHER PUBLICATIONS

"Solution auto-stable pour les fusions intersomatiques par voie anterieure", Synthes, 1 page.

*Primary Examiner* — Eduardo C Robert
*Assistant Examiner* — Jerry Cumberledge

(57) ABSTRACT

An implantable medical device may include an implant member having an aperture extending therethrough. An anchor member may be configured to extend through the aperture. A locking ring may be supplied to inhibit back-out of the anchor member.

25 Claims, 6 Drawing Sheets

ANCHOR MEMBER LOCKING FEATURES

FIELD OF THE INVENTION

The present invention relates generally to the field of medical implants secured by anchor members.

BACKGROUND

Spinal discs between the endplates of adjacent vertebrae in a spinal column of the human body provide critical support. However, due to injury, degradation, disease or the like, these discs can rupture, degenerate and/or protrude to such a degree that the intervertebral space between adjacent vertebrae collapses as the disc loses at least a part of its support function. This can cause impingement of the nerve roots and severe pain. In some cases, surgical correction may be required.

Some surgical corrections include the removal of the natural spinal disc from between the adjacent vertebrae. In order to preserve the intervertebral disc space for proper spinal-column function, an implant member can be inserted between the adjacent vertebrae.

Some implant members employ anchor members that fix the implant member in place between the adjacent vertebrae. Over time, due to micro motion of the vertebrae relative to the implant member, the anchor members may loosen and start to back-out of vertebrae. In addition to possibly allowing the implant member to become loose and potentially displace within the vertebral space, the anchor members themselves may protrude and cause damage to sensitive tissue and organs in the patient.

What is needed is an implantable device that reduces or eliminates anchor member back-out. The implantable devices disclosed herein address one or more deficiencies in the art.

SUMMARY

In one exemplary aspect, an implantable medical device is disclosed. It may include an implant member having an aperture extending therethrough. The aperture may include an inner surface having an integral inwardly extending elastically deformable locking ring having a first diameter. The device also may include an anchor member configured to extend through the aperture. The anchor member may include a head portion having a second diameter greater than the first diameter. The locking ring and the anchor member may be configured in a manner that allows the anchor member to pass in a first direction and restricts passage in an opposite second direction.

In another exemplary aspect, an implantable medical device is disclosed. The device may include an implant member having an aperture extending therethrough. The aperture may have an inner surface and may have a semicircular channel formed in the inner surface. The semicircular channel may have end boundary walls. The device also may include a semicircular locking ring disposed in the semi-circular channel. The end boundary walls may be configured to limit rotation of the locking ring in the semicircular channel.

In another exemplary aspect, an implantable medical device is disclosed. The device may include an implant member including an aperture extending there through. The aperture may have an inner surface and may have an implant member channel formed in the inner surface. An anchor member may be configured to be inserted into the aperture. The anchor member may include an anchor member channel formed therein. A locking ring may be disposed within the anchor member channel. The locking ring may have a cross-section that fits within the implant member channel and also may permit removal of the anchor member from the implant member.

In yet another exemplary aspect, a method of implanting an implantable medical device is disclosed. The method may include introducing an implant member into a disc space formed between two adjacent vertebrae. The implant member may have an aperture formed therein, the aperture having an inner surface. The method also may include introducing an anchor member into the aperture so that the anchor member engages a bearing endplate of one of the vertebrae. The anchor member may have an outer surface. A locking ring may be deformed from a neutral condition by contacting the locking ring against one of: the inner surface of the aperture, and the outer surface of the anchor member. Back-out of the anchor member may be physically inhibited by allowing the locking ring to at least partially deflect toward the neutral condition.

Further aspects, forms, embodiments, objects, features, benefits, and advantages of the present invention shall become apparent from the detailed drawings and descriptions provided herein.

DETAILED DESCRIPTION

Figure 1:
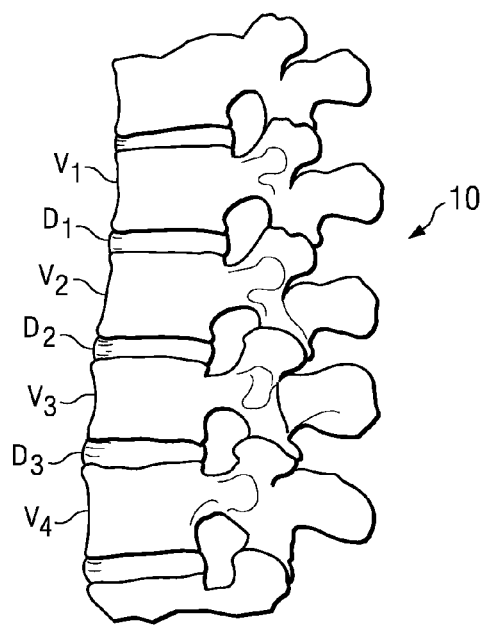
FIG. 1 is an illustration of a lateral view of a segment of a lumbar spine.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a lateral view of a portion of a spinal column 10, illustrating a group of adjacent upper and lower vertebrae V1, V2, V3, V4 separated by natural intervertebral discs D1, D2, D3. The illustration of four vertebrae is only intended as an example. Another example would be a sacrum and one vertebra.

Figure 2:
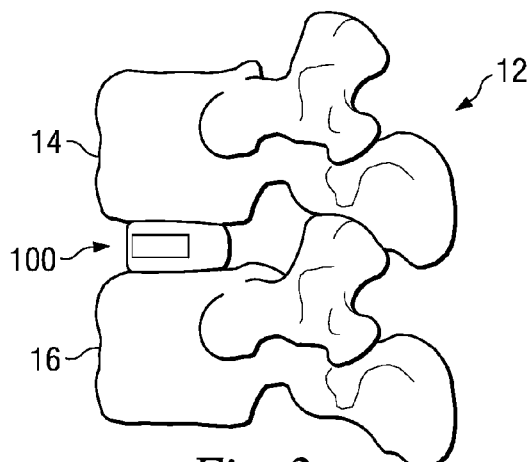
FIG. 2 is an illustration of a lateral view of a spinal segment formed by two vertebrae with an exemplary implantable device disposed therebetween.

For the sake of further example, two of the vertebrae will be discussed with reference to a spinal segment 12 shown in FIG. 2. An upper vertebra 14 and a lower vertebra 16, which may be any of the vertebrae V1, V2, V3, V4, define the spinal segment 12. Although the illustrations of FIGS. 1 and 2 generally depict a lumbar vertebrae and a lumbar vertebral segment, it is understood that the devices, systems, and methods of this disclosure may also be applied to all regions of the vertebral column, including the cervical and thoracic regions.

Some types of disc arthroplasty require that some or the entire natural disc that would have been positioned between the two vertebrae 14, 16 be removed via a discectomy or a similar surgical procedure. Removal of the diseased or degenerated disc results in the formation of an intervertebral space between the upper and lower vertebrae 14, 16. Once the diseased or degenerated disc is removed, an implantable prosthetic device may be used to maintain the vertebral spacing and provide vertebral support. As shown in FIG. 2, an implantable device, referenced herein by the reference numeral 100, resides within the vertebral space. Sized to fit the disc space height in a manner similar to a natural intervertebral disc, such as any of discs D1-D4, the implantable device 100 provides support and stabilization to the vertebrae.

Figure 3:
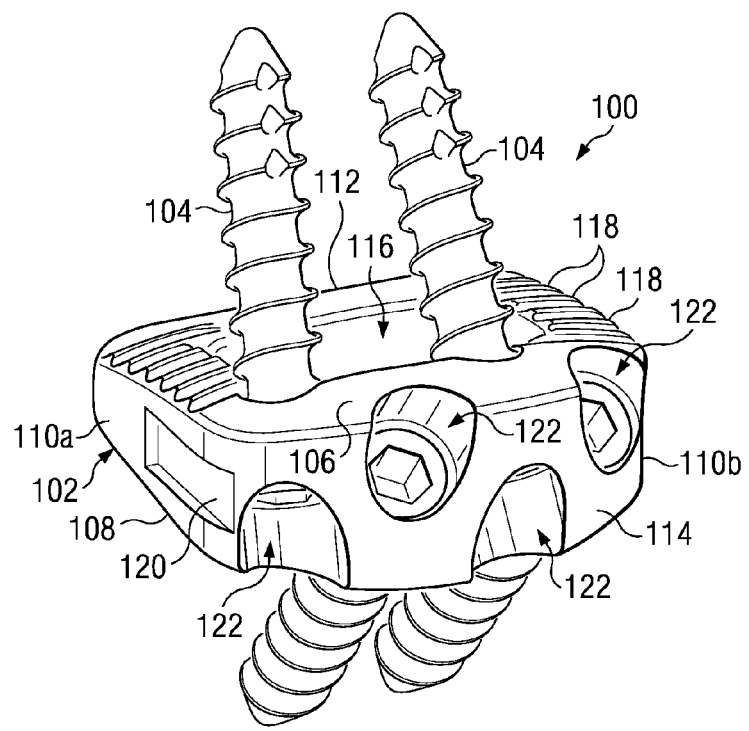
FIG. 3 is an illustration of a perspective view of one exemplary embodiment of the implantable device shown in FIG. 2.
Figure 4:
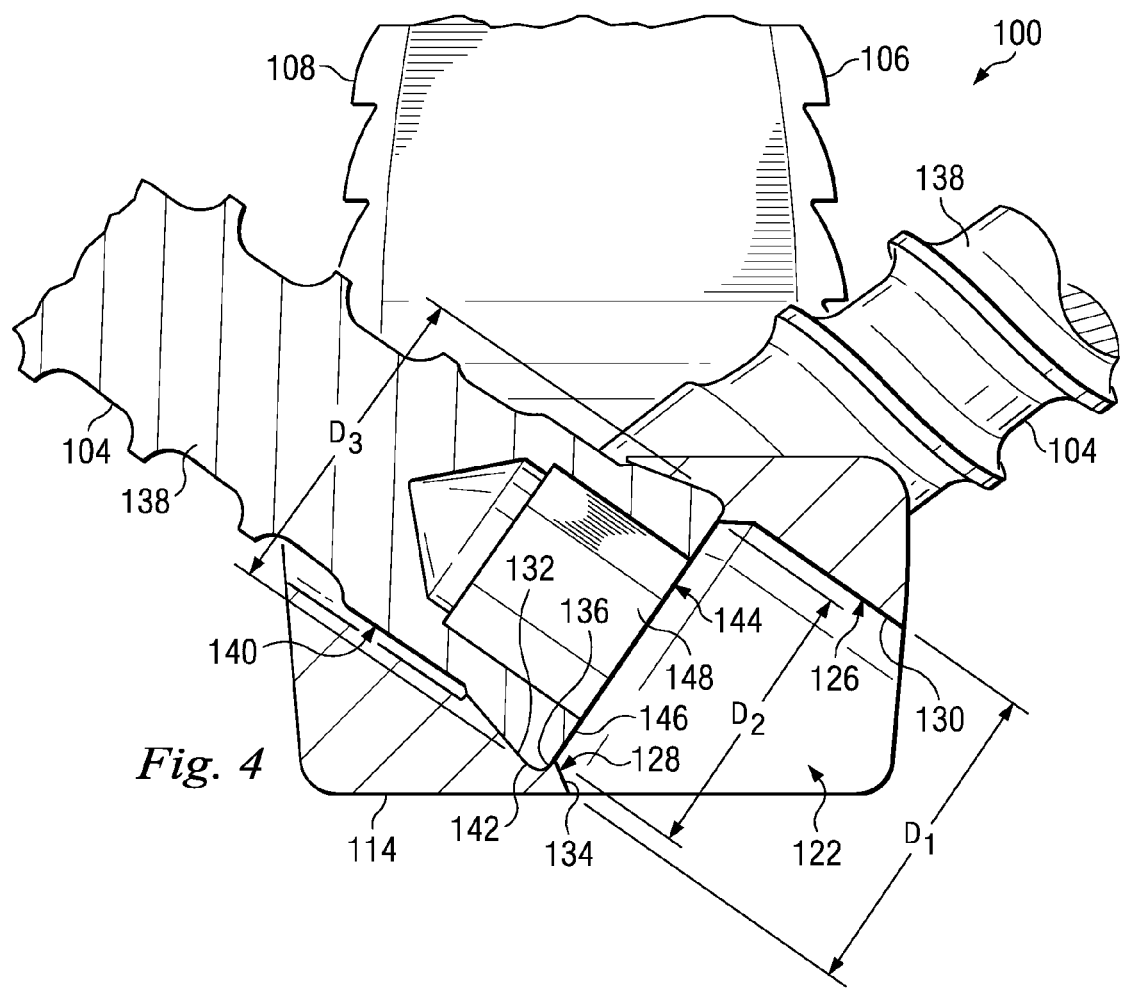
FIG. 4 is an illustration of a cross-sectional view of the exemplary implantable device shown in FIG. 3.

FIGS. 3 and 4 show the implantable device 100 in greater detail. FIG. 3 shows a perspective view of the implantable device 100, while FIG. 4 shows a cross-sectional view of the implantable device 100. Referring now to both FIGS. 3 and 4, the implantable device includes an implant member 102, such as a spacer, and one or more anchor members 104. The implant member 102 may include an upper surface 106, a lower surface 108, side surfaces, 110a-b, a rear surface 112 and an front surface 114. The upper and lower surfaces 106, 108 may be configured to interface with the bearing endplates of the upper and lower vertebrae 14, 16 as shown in FIG. 2, while the side, rear, and front surfaces 110a-b, 112, 114 extend between the upper and lower surfaces 106, 108. In this exemplary embodiment, the front surface is an anterior surface and the rear surface is a posterior surface. However, the front and rear surfaces are relative and may be face any direction within the disc space. A hollow center 116 may allow placement of bone growth materials, such as allograft to promote bonding and fusion of the implantable device 100 to the adjacent vertebrae.

In the embodiment shown, the upper and lower surfaces 106, 108 include bone engaging features 118 configured to reduce slipping or movement of the implant member 102 relative to vertebrae 14, 16. In the exemplary embodiment shown, the bone engaging features 118 are angled teeth that permit introduction into the disc space, but also restrict removal. The side surfaces 110a-b each include a recessed slot 120 configured to cooperate with an insertion tool (not shown) that selectively connects to the implant member 102. In some embodiments, within the slot 120, connecting impressions (not shown) may be configured to provide a secure connection with the insertion tool.

The front surface 114 includes apertures 122 that receive anchor members 104 for attaching the implant member 102 to the vertebral bodies 14, 16. In this exemplary embodiment, the anchor members 104 are bone screws. However, other anchor members are contemplated. The anchor members 104 extend through the front surface 114 and out the hollow center 116 and into the bearing endplates of the vertebrae 14, 16, thereby securely locating the implant member 102 entirely within the disc space. In this exemplary embodiment, the implant member 102 includes four apertures 122—two angled to allow anchor members 104 to attach to an upper vertebral endplate and two angled to allow anchor members 104 to attach to a lower vertebral endplate, as best seen in FIG. 3. This allows the anchor members 104 to penetrate the bearing endplates of the vertebral bodies. In addition, when the implantable device 100 is a spacer as shown in FIG. 2, it is capable of being entirely contained within the disc space. Accordingly, anchor member locking features that reduce the chance of anchor member back-out, also may be disposed entirely within the disc space. This reduces a chance of creating additional patient trauma that may occur if organs and tissue are able to easily contact the implantable device outside the disc space.

To reduce the chance of the anchor members 104 backing out of the vertebral bodies over time and causing the implant member 102 to become loose, the apertures 122 each include an inner surface 126 with an integral inwardly extending locking ring 128, shown best in FIG. 4. The aperture inner surface 126 is formed to have a first surface portion 130 defining a first diameter D1 and a second surface portion 132 that tapers inwardly. When in a neutral or unloaded condition, the locking ring 128 defines a second inner diameter D2 that is smaller than the first diameter D1 of the inner surface 126. In the embodiment shown, a leading tapered surface 134 and a trailing locking surface 136 together form the locking ring 128. The leading tapered surface 134 creates a gradual decrease in size of the aperture 122, while the trailing locking surface 136 extends from and is substantially perpendicular to the inner surface 126, forming a lip or shoulder. Other shapes at other angles also are contemplated.

The locking ring 128 may be constructed in whole or in part of biocompatible materials of various types. Examples of locking ring materials include, but are not limited to, reinforced or non-reinforced polymers, carbon-reinforced polymer composites, PEEK and PEEK composites, shape-memory alloys, titanium, titanium alloys, cobalt chrome alloys, stainless steel, ceramics and combinations thereof. Polymer and composites may be particularly well-suited for forming the locking ring 128 because of their compliant properties, as the compliant protruding locking ring 128 may elastically deform or yield when the anchor member 104 is inserted into the aperture 122, as described further below. In other embodiments, the locking ring, or other components of the implantable device 100 may be formed of a shape memory material or a super elastic material.

The anchor member 104 includes a threaded body portion 138 and a head portion 140, as shown in FIG. 4. The head portion 140 includes a tapering surface 142 and a tool receiving end 144 having an end surface 146 and a tool receiving bore 148. The tapering surface 142 leads to an outermost diameter D3 that is greater than the second inner diameter D2 of the locking ring D2 when the locking ring 128 is in a neutral or unloaded condition, but smaller than the first diameter D1 of the first surface portion 130 of the aperture 122.

The implantable device 100 may be implanted in a properly prepared spinal column to provide support and stability to the column. In some embodiments, the implant member 102 may be placed in a prepared disc space between adjacent vertebrae so that the upper and lower surfaces 106, 108 contact bearing endplates of the vertebral bodies. Once positioned, one of the anchor members 104 may be introduced through one of the apertures 122 in the implant member 102, and then rotated to engage with and advance into one of the vertebral endplates. As the anchor member 104 advances through the aperture 122, the tapering surface 142 of the head portion 140 engages and slides against the leading tapered surface 134 of the locking ring 128. Further advancement may cause the compliant locking ring 128 to deform slightly or yield to allow passage of the anchor member head portion 140. Once the anchor member head portion 140 passes the locking ring 128, the locking ring 128 may at least partially deform back to its original condition, so that its inner diameter D2 is smaller than the anchor member head portion diameter D3. The locking ring 128, with its smaller diameter, inhibits anchor member back-out because the trailing locking surface 136, physically obstructs back-out movement of the anchor member 104. As the anchor member 104 further advances, the tapering surface 142 of the head portion 140 contacts and pushes against the second surface portion 132 of the inner surface 126 to secure the implant member 102 and the entire implantable device 100 in place.

Although shown as an annular projecting ring in FIGS. 3 and 4, in other embodiments, the locking ring 128 is formed of a plurality of spaced protrusions that together operate similar to the annular locking ring 128 described above. For example, in one embodiment, the locking ring 128 is defined by four protrusions equally spaced about the inner surface 126. Other arrangements also are contemplated. In some alternate embodiments, the anchor member head portion 140 is compliant while the locking ring 128 is rigid, such as may occur when an anchor member formed at least partially of a yielding material, such as a polymer, is used with a titanium implant member. In these embodiments, the head portion slightly deforms as the anchor member is driven past the locking ring, and once past, at least partially elastically deforms so that the locking ring interferes with the head portion to prevent anchor member back-out. In yet other embodiments, both the anchor member head portion 140 and the locking ring 128 are compliant, such as when they are formed of a similar material, such that they both deform slightly so that the anchor member head portion 140 can advance past the locking ring 128.

Figure 5:
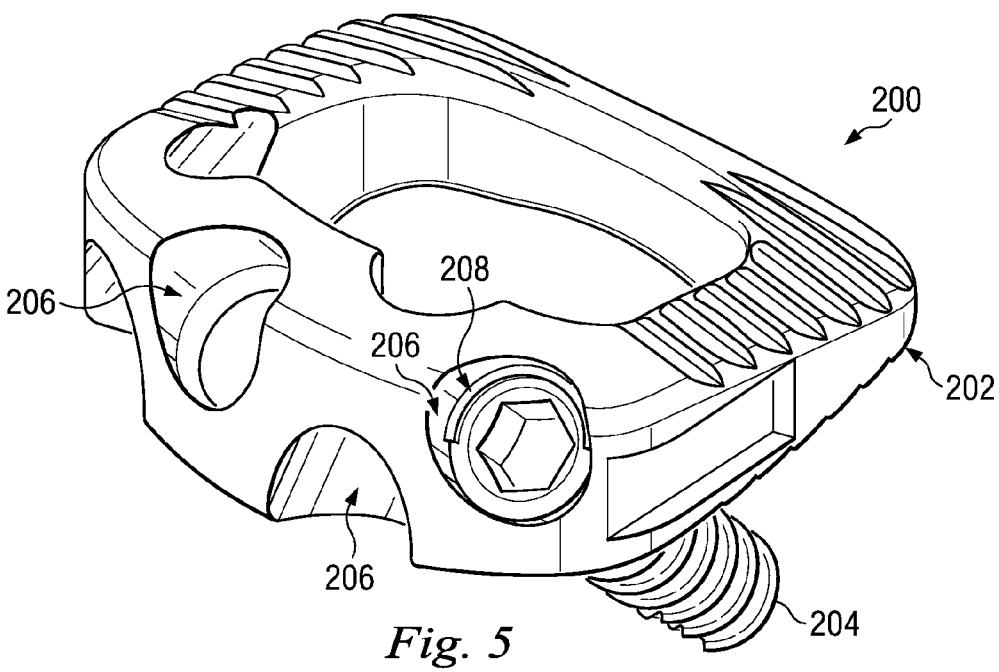
FIG. 5 is an illustration of a perspective view of another exemplary embodiment of an implantable device.

FIGS. 5-8 show another embodiment of an implantable device, generally referenced herein by the reference numeral 200. Similar to the device described above, the implantable device in this embodiment includes an implant member 202 shown as a spacer, and an anchor member 204. The implant member 202 may include any of the features of the implant member 102 described above, including apertures for receiving the anchor members, referenced with respect to this embodiment as 206. Although only one anchor member 204 is shown in FIG. 5, it should be understood that this is for ease of explanation and that two, three, four or more anchor members 204 may be used to secure the implant member 202 in place between the upper and lower vertebrae 14, 16 depending on the number of apertures 206.

Figure 6:
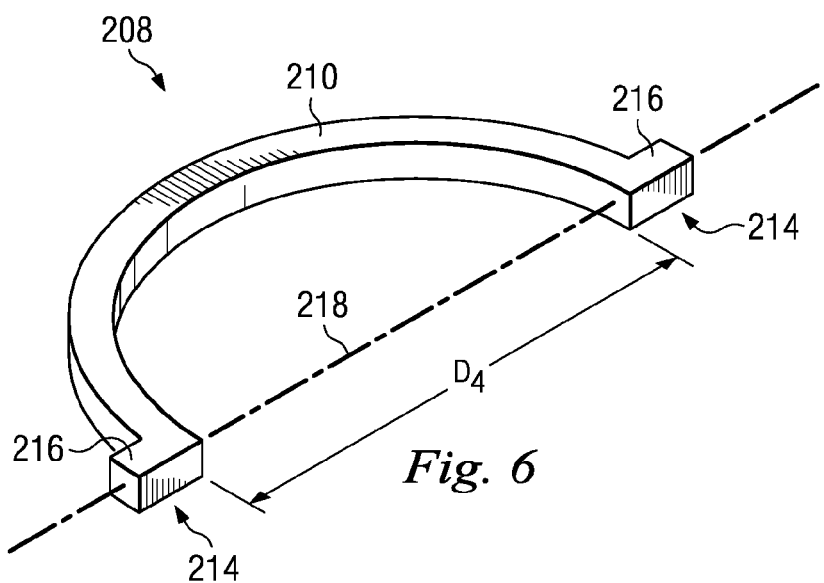
FIG. 6 is an illustration of a perspective view of an exemplary locking ring forming a part of the implantable device shown in FIG. 5.

In this embodiment, a locking ring 208, configured to inhibit anchor member back-out, is disposed within each aperture 206. One exemplary embodiment of the locking ring 208 is shown in FIG. 6. Here, the locking ring 208 is semicircular shaped and includes an arcing body 210 having a first end 212 and a second end 214, shown best in FIG. 6. At each end 212, 214, outwardly protruding portions 216 help secure the locking ring 208 in the aperture 206. In the embodiment shown, the protruding portions 216 extend in opposite directions along an axis 218. Although the semicircular locking ring 208 is shown as a half-circle, it is understood that the term "semicircular" is intended to include rings that are more than or less than a half-circle. In some exemplary embodiments, the locking ring 208 may be formed of a spring-type material that is capable of at least partial elastic deformation. In other embodiments, the locking ring may be formed of a shape memory material, a metal such as titanium or stainless steel for example, a polymer material, among others. In some embodiments, the locking ring 208 is a snap ring configured to have a first inner diameter D4 when in a first neutral condition, is configured to expand to a second larger inner diameter when the anchor member 204 is inserted into the aperture 206 and driven through the locking ring 208, and is configured to at least partially elastically return to its neutral condition.

Figure 7:
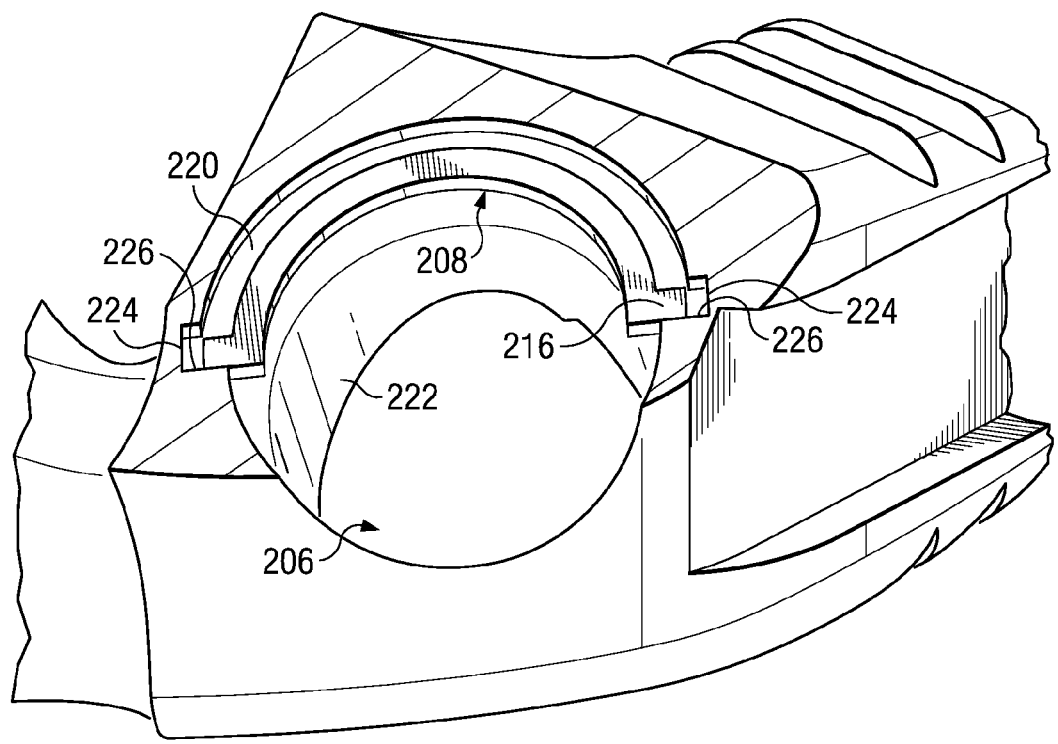
FIG. 7 is an illustration of a cross-sectional view of a portion of the implantable device shown in FIG. 5.

FIG. 7 shows a cross-sectional view of a part of the implantable device 100 with the locking ring 208 disposed within a channel 220 formed within the aperture 206 of the implant member 202. As shown, the aperture 206 includes an inner surface 222 with the channel 220 formed therein and outwardly extending therefrom. The channel 220 includes slots 224 formed therein and has a depth that allows the locking ring 208 to expand within the channel 220 when required. When placed within the channel 220, the protruding portions 216 of the locking ring 208 are configured to fit within the slots 224 to reduce the chance of the locking ring 208 disengaging from the channel 220. In addition, the channel 220 includes boundary walls 226 that limit the amount of locking ring rotation within the aperture 206, holding the semicircular locking ring 208 in place.

In the embodiment shown in FIG. 7, the cross-section, taken through the channel 220 substantially perpendicular to an axis formed by the aperture 206, intersects only a part of the angled aperture 206. Because of the angle, the remaining part is not cross-sectioned. Accordingly, the channel 220 is formed at a depth within the angled aperture 206 that does not allow a complete circumferential channel to be contained within the implant member 202. Therefore, in this exemplary embodiment, the channel 220 and the locking ring 208 are formed to be semicircular so that they may be disposed entirely within the aperture 206 of the implant member 202. It is understood however, that the channel 220 may be formed within the aperture 206 at any desired depth, including a depth that allows a full circumferential channel to extend about the inner circumference of the aperture 206.

Figure 8:
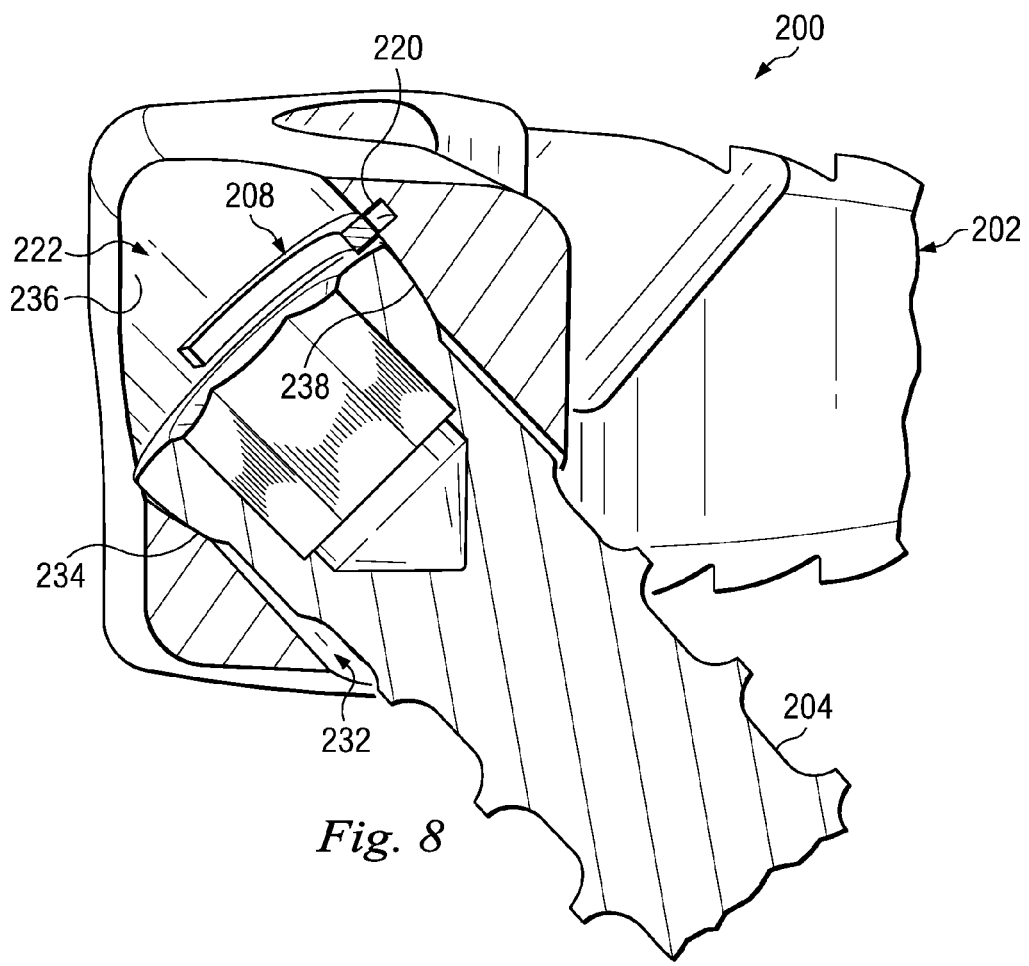
FIG. 8 is an illustration of another cross-sectional view of a portion of the implantable device shown in FIG. 5.

FIG. 8 shows a cross-sectional view of the implant member 202 and locking ring 208 with the anchor member 204 in place. As can be seen, the anchor member 204 may be substantially similar to the anchor member 104 described above, having an anchor member head portion 232 with a tapering surface 234. The inner surface 222 of the aperture 206 includes a first surface portion 236 and a second surface portion 238. The first surface portion 236 may be formed substantially cylindrically, while the second surface portion 238 may include a narrowing taper or conical shape that interfaces with the tapering surface 234 of the anchor member 204 to secure the implant member 202 in place against the vertebrae. This is because the anchor member 204 has a greater diameter than an inner diameter of the locking ring 208 in its neutral condition. Here, the anchor member 204 has a geometry that interacts with the locking ring 208 to expand the locking ring 208 while inserting the anchor member 204. For example, when inserted into the aperture 206, the tapering surface 234 of the anchor member head portion 232 deforms the locking ring 208 by forcing it to outwardly deflect into the channel 220 formed within the inner surface 222 of the aperture 206. Once the anchor member head portion 232 passes, the locking ring 208 springs back into place behind the anchor member head portion 232, thereby physically inhibiting any undesired anchor member back-out.

Although shown as a single locking ring in FIGS. 7 and 8, in other embodiments, the locking ring 208 may comprise two or more locking rings used to cooperatively interact with sides, such as opposing sides, of the anchor member head portion 232 to inhibit back-out. Further, although shown as extending about fifty percent of the way around the head portion 232, in other embodiments, the locking ring 208 extends between about twenty-five and seventy-five percent of the distance around the anchor member head portion 232. In yet other embodiments the locking ring 208 extends between about thirty and sixty percent of the distance around the anchor member head portion 232. In embodiments extending less than fifty percent of the distance around the anchor member, a radius of the curve may be measured and doubled to obtain the diameter.

Figure 9:
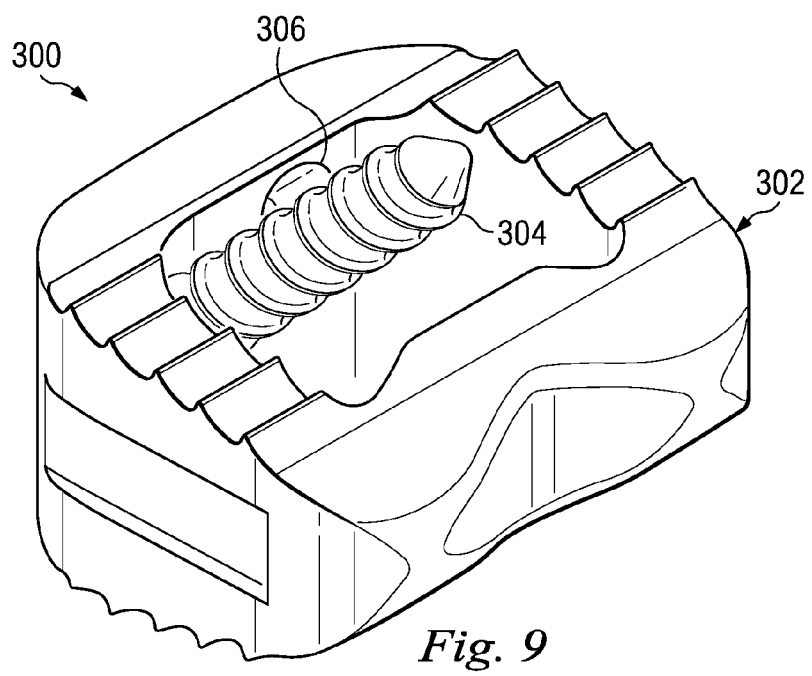
FIG. 9 is an illustration of a perspective view of yet another exemplary embodiment of an implantable device.

FIG. 9 shows yet another embodiment of an implantable device. This embodiment of the implantable device is referenced herein by the reference numeral 300. The implantable device 300 may include an implant member 302, such as a spacer, and anchor members 306. In this embodiment, only one anchor member 304 is shown, although others are contemplated, as mentioned above. The implant member 302 may include any of the features of other embodiments described herein, including apertures, referenced in this embodiment by the reference numeral 306.

Figure 10:
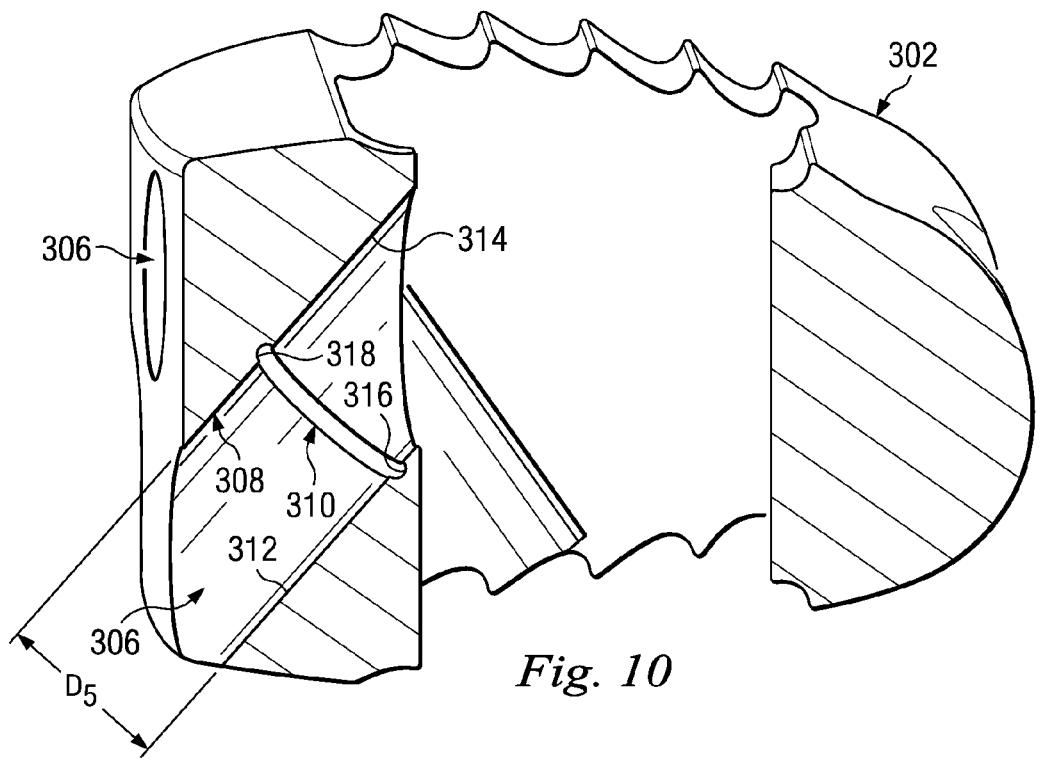
FIG. 10 is an illustration of a cross-sectional view of a portion of the implantable device shown in FIG. 9.

Turning to FIG. 10 a cross-sectional view of the implant member 302 taken through one of the apertures 306 shows an inner surface 308 having a channel 310 formed therein. The inner surface 308 includes a first surface portion 312 and a second surface portion 314. In this embodiment, the first surface portion 312 in this embodiment may be slightly tapered or conically shaped, while the second surface portion 314 also may be slightly tapered or conically shaped, and in some embodiments may have an angle different than the first surface portion. Adjacent the channel 310, the first surface portion 312 may have a diameter D5. The channel 310 in this exemplary embodiment is disposed between the surface portions 312, 314 and may be formed as a substantially annular ring having a U-shaped inner channel surface 316 with a rear locking wall 318 configured to engage a locking ring, as explained below.

Figure 11:
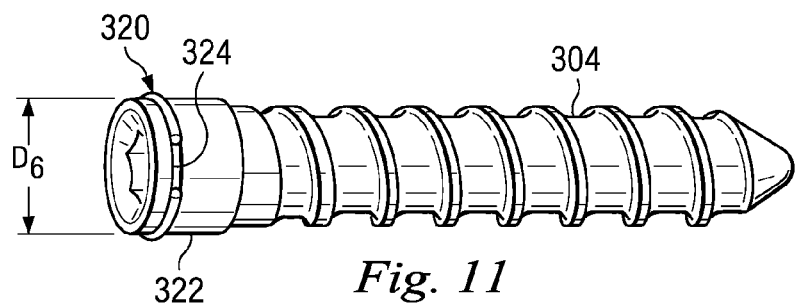
FIG. 11 is an illustration of a perspective view of an anchor member forming a part of the implantable device shown in FIG. 9.

FIG. 11 shows an exemplary anchor member 304 with an associated locking ring 320. The anchor member 304 may include any of the features described in other embodiments, but here also includes a head portion 322 having a ring channel 324 formed therein. The channel 324 is a U-shaped channel configured to fit the locking ring 320 at least partially therein. The head portion 322 defines an outer diameter D6 in the region the channel 324 is located.

Figure 12:
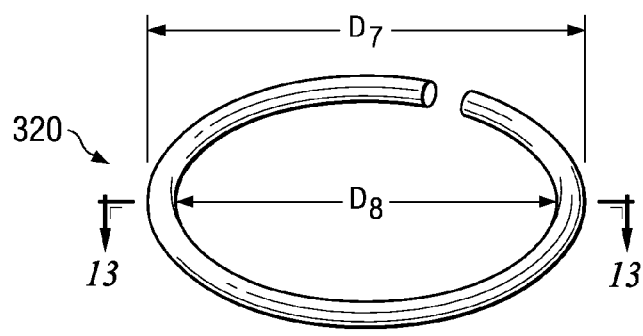
FIG. 12 is an illustration of a perspective view of an exemplary locking ring forming a part of the implantable device shown in FIG. 9.
Figure 13:
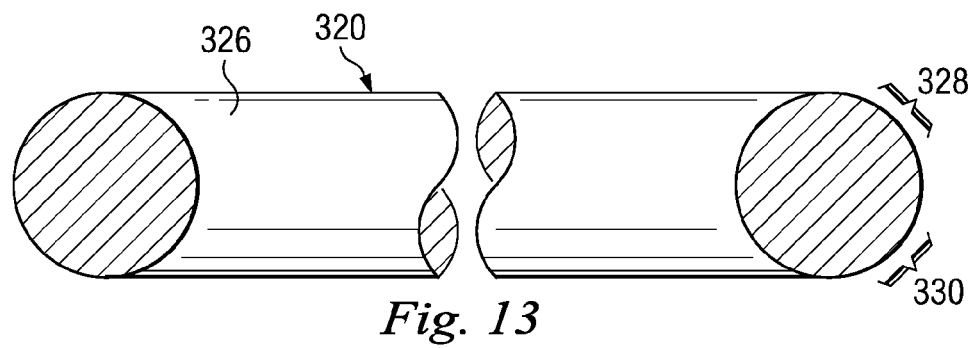
FIG. 13 is an illustration of a cross-sectional view of the locking ring shown in FIG. 12.

The locking ring 320 is shown in greater detail in FIGS. 12 and 13. The locking ring 320 in this embodiment may be a compressible snap ring that has a first outer diameter D7 and a first inner diameter D8 in a neutral or uncompressed condition, but that is compressible to a second or smaller diameter. The neutral outer diameter D7 of the locking ring 320 is greater than the diameter D6 of the head portion 322 and greater than the inner surface diameter D5 of the aperture 306. Likewise, the neutral inner diameter D8 of the locking ring 320 is less than the diameter D6 of the head portion 322 and less than the inner surface diameter D5 of the aperture 306. Thus, the locking ring 320 is sized to simultaneously extend into the head portion channel 324 and the aperture channel 216.

An outer surface 326 of the locking ring 320 may include a leading contact region 328 configured to contact the aperture inner surface 308 (FIG. 10) when the anchor member 304 is being driven into the aperture 306. It also may include a trailing contact region 330 configured to engage the rear locking wall 318 (FIG. 10) of the aperture channel 310 when the anchor member 304 is being removed or when the anchor member 304 begins to experience back-out. In this embodiment, the trailing contact region 330 cooperates with the aperture channel 310 to inhibit back-out. In addition, because of its shaped cross-section including the rounded trailing contact region 330, the anchor member 304 is capable of being removed manually from the implant member 302, if desired, by turning the anchor member 304 until the locking ring 320 engages the rear locking wall 318 of the aperture channel 310, and until the force deflects the locking ring 320 into the anchor member channel 324 and entirely out of the aperture channel 310. Thus, the anchor member 304 not only inhibits back-out, but also can be removed more easily than prior locking designs. Although shown as having a round or circular cross-section, in other embodiments the cross section of the locking ring 320 is oval shaped, D-shaped, triangular shaped, among others. Therefore, in some embodiments, as described above, the trailing contact region 330 may be rounded or tapered to engage the rear locking wall 318 to promote securing of the anchor member 304 within the aperture, but also may be shaped, such as rounded or tapered to slide over and disengage the rear locking wall 318 to allow removal of the anchor member 304 from the aperture 306. Yet other cross-sectional shapes are contemplated.

Figure 14:
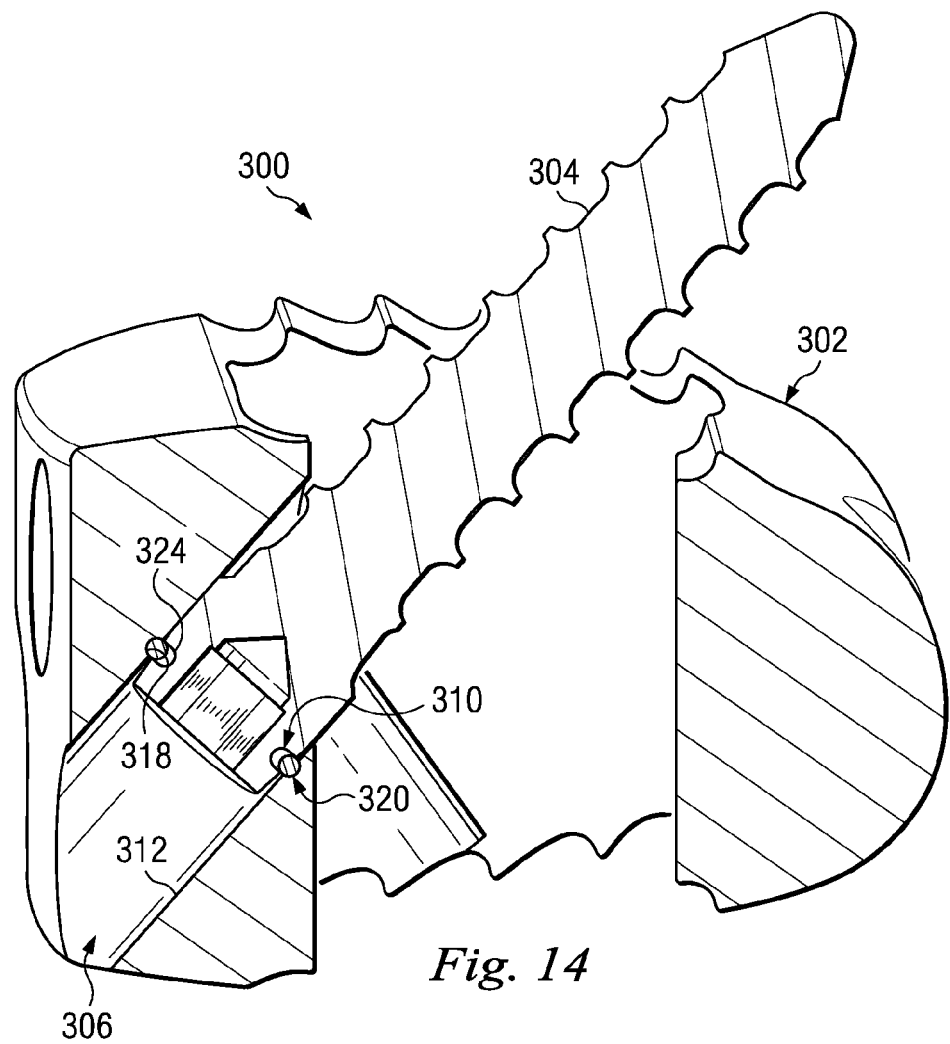
FIG. 14 is an illustration of another cross-sectional view of the implantable device shown in FIG. 9.

FIG. 14 shows the anchor member 304 and locking ring 320 engaged in the implant member 302. When inserting the anchor member 304, the tapered first surface portion 312 of the inner surface 308 of the implant member 302 compresses the locking ring 320 into the anchor member head channel 324, decreasing the locking ring diameter. When inserted to the aperture channel 310, the locking ring 320 at least partially snaps back to a larger diameter, thereby engaging both the anchor member channel 324 and the aperture channel 310. In this condition, the locking ring 320 inhibits anchor member back-out. If desired, the anchor member 304 can still be removed from the implant member 302 by unscrewing the anchor member 304 until the rear locking wall 318 of the channel 310 interfaces with the trailing contact region 330 of the locking ring 320 and its outer shape forces the locking ring 320 to compress inwardly and slip out of the aperture channel 310 and more fully into the anchor member channel 324, thereby disengaging the locking ring 320 from the aperture channel 310.

Some embodiments of the implantable devices disclosed herein employ radiopaque materials that allow locations of the components of the implantable devices to be tracked. For example, in some embodiments, the locking ring may be formed of a radiopaque material. In other embodiments, other components may be formed of radiopaque materials.

In some embodiments, the implantable devices disclosed herein or individual components of the implantable devices are constructed of solid sections of bone or other tissues. Further, in some circumstances, it is advantageous to pack the hollow center of any of the implant members with a suitable osteogenetic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device can also be used. These carriers can include collagen-based carriers, bioceramic materials, such as BIO-GLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack the interior of the implant member with material and then place it within the disc space.

Access to the surgical site may be through any surgical approach that will allow adequate visualization and/or manipulation of the bone structures. Example surgical approaches include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated.

It is understood that all spatial references, such as "top," "inner," "outer," "bottom," "left," "right," "anterior," "posterior," "superior," "inferior," "medial," "lateral," "upper," "lower," "front," and "rear" are for illustrative purposes only and can be varied within the scope of the disclosure.

While embodiments of the invention have been illustrated and described in detail in the disclosure, the disclosure is to be considered as illustrative and not restrictive in character. All changes and modifications that come within the spirit of the invention are to be considered within the scope of the disclosure.

We claim:

1. An implantable medical device, comprising:
   an implant member having an upper surface configured to interface with a bone structure, a lower surface configured to interface with a bone structure, and a side surface extending from the upper surface to the lower surface, the implant member also having an angled aperture extending through the side surface, the aperture having an axis and having an inner surface with a semicircular channel formed in the inner surface, the channel being disposed in a plane substantially normal to the axis and disposed at a depth within the angled aperture where the plane intersects with the inner surface along a partial circumferential line and not a complete circumferential line, the semicircular channel being formed by first and second sidewalls and end boundary walls, the end boundary walls forming ends of the channel and being disposed on substantially opposing sides of the aperture; and
   a semicircular locking ring disposed in the semi-circular channel and being sized to extend about to the end boundary walls of the channel, the locking ring having an upper surface and a lower surface, the upper surface being disposed to face the first side wall of the channel and the lower surface being disposed to face the second sidewall of the channel, wherein the end boundary walls are configured to limit rotation of the locking ring in the semicircular channel, the locking ring being configured to cooperate with the implant member to prevent back-out of an anchor member in the aperture.

2. The device of claim 1, further comprising:
   an anchor member configured to extend through the aperture, the anchor member having a geometry that interacts with the locking ring to expand the locking ring while inserting the anchor member.

3. The device of claim 1, wherein the ring is elastically deformable in a manner that allows an anchor member to pass in a first direction and restrict passage in an opposite second direction.

4. The device of claim 1, wherein the channel includes a first portion having a first depth and a slot formed therein having a second depth different than the first depth, and wherein the ring includes a protruding portion configured to fit within the slot.

5. The device of claim 4, wherein the locking ring includes a first and a second end, the protruding portion being a first protruding portion at the first end and further including a second protruding portion at the second end.

6. The device of claim 1, wherein the locking ring has a first inner diameter while in a neutral condition, the device comprising an anchor member including a head portion having a second diameter greater than the first diameter of the locking ring.

7. The device of claim 1, wherein the channel is disposed within the aperture so that a cross-section through the inner surface intersects only a part of the inner surface.

8. The device of claim 1, wherein the locking ring is entirely contained within the aperture.

9. The device of claim 1, wherein the implant member is a spacer sized for placement between adjacent vertebrae.

10. The device of claim 9, wherein the aperture is aligned in the implant member so that an anchor member in the aperture is aligned to penetrate a bearing surface of a vertebral body.

11. The device of claim 1, wherein the implant member and the locking ring are configured to fit entirely within the disc space.

12. An implantable medical device, comprising:
    an implant member having a front surface, upper and lower bearing surfaces, and an aperture extending through the front surface toward one of the upper and lower bearing surfaces, the aperture having an axis and having an inner surface and having a channel formed in the inner surface, the channel being disposed in a plane substantially normal to the axis and disposed at a depth within the aperture where the plane intersects with the inner surface along a partial circumferential line and not a complete circumferential line, the implant having at least one radially projecting slot in the channel; and
    a locking ring disposed in the channel, the locking ring having at least one protruding portion that extends into the radially projecting slot, the locking ring being configured to cooperate with the implant member to prevent back-out of a bone screw in the aperture.

13. The device of claim 12, wherein the slots are sized to permit the locking ring to expand within the channel.

14. The device of claim 12, wherein the channel and the locking ring are semi-circular.

15. The device of claim 12, further comprising:
    an anchor member configured to extend through the aperture, the anchor member having a geometry that interacts with the locking ring to expand the locking ring while inserting the anchor member.

16. The device of claim 12, wherein the ring is elastically deformable in a manner that allows an anchor member to pass in a first direction and restrict passage in an opposite second direction.

17. The device of claim 12, wherein the locking ring includes a first and a second end, the protruding portion being a first protruding portion at the first end and further including a second protruding portion at the second end.

18. An implantable medical device, comprising:

an implant member having an upper surface configured to interface with a bone structure, a lower surface configured to interface with a bone structure, and a side surface extending from the upper surface to the lower surface, the implant member also having an angled aperture extending through the side surface, the aperture having an axis and having an inner surface with a semicircular channel formed in the inner surface, the channel being disposed in a plane substantially normal to the axis and disposed at a depth within the angled aperture where the plane intersects with the inner surface along a partial circumferential line and not a complete circumferential line, the channel having a first end and a second end, the first and second ends being located on substantially opposing sides of the aperture, each of the first and second ends forming boundary walls, the channel including a channel bottom surface, and including slots formed in the channel bottom surface at the first and second ends, the slots extending radially outward from the channel bottom surface to have a depth greater than the depth of the channel bottom surface;

a semicircular locking ring extending substantially from the first end of the channel to the second end of the channel, at least a portion of the locking ring being disposed within the channel and at least a portion of the locking ring being disposed outside the channel in the aperture, the locking ring having first and second ends that outwardly protrude and fit within the slots in the channel, the locking ring being configured to cooperate with the implant member to prevent back-out of an anchor member in the aperture; and an anchor member configured to extend through the aperture, the anchor member having a geometry that interacts with the locking ring to expand the locking ring so that the first and second ends of the locking ring protrude more deeply into the respective first and second slots while inserting the anchor member.

19. The device of claim 18, wherein the ring is elastically deformable in a manner that allows an anchor member to pass in a first direction and restrict passage in an opposite second direction.

20. The device of claim 18, wherein the locking ring has a first inner diameter while in a neutral condition, the anchor member including a head portion having a second diameter greater than the first diameter of the locking ring.

21. The device of claim 18, wherein the channel is disposed within the aperture so that a cross-section through the inner surface intersects only a part of the inner surface.

22. The device of claim 18, wherein the implant member is a spacer sized for placement between adjacent vertebrae.

23. The device of claim 18, wherein the aperture is aligned in the implant member so that an anchor member in the aperture is aligned to penetrate a bearing surface of a vertebral body.

24. The device of claim 18, wherein the implant member and the locking ring are configured to fit entirely within the disc space.

25. The device of claim 18, wherein the locking ring includes a planar upper surface and a parallel planar lower surface.

* * * * *